Nov. 8, 1955 D. D. ABBOTT Plant Pat. 1,431

ABELIA PLANT

Filed Sept. 8, 1953

INVENTOR,
DELVAN D. ABBOTT
BY
D. Gordon Angus

United States Patent Office

Plant Pat. 1,431
Patented Nov. 8, 1955

1,431

ABELIA PLANT

Delvan D. Abbott, San Marino, Calif.

Application September 8, 1953, Serial No. 379,105

1 Claim. (Cl. 47—59)

The present invention relates to a new variety of the shrub abelia, which shrub having the botanical name *Caprifoliaceae Abelia grandiflora,* of the order Rubiaceae, commonly grows to a height of from 5 to 7 feet in an upright bush-like fashion.

The present new or improved variety is characterized by its low growth, growing to a height of only about 2 feet and by its prostrate or trailing habit, spreading to a width of about 3½ feet, and by other characteristics as hereinafter set forth in the detailed description of the new variety.

In my work as an overseer or foreman of parks I handle and develop many plants with the object of producing the same in the best form and appearance and in such work I am also always on the lookout for any new developments and such activity is also carried on as personal or private project as well as in connection with my regular employment.

In 1949 I observed on my property a sport or mutation growth on a conventional abelia shrub.

From such sport or mutation a carefully prepared cutting was taken and rooted and asexual reproductions were reproduced therefrom.

About 200 asexually reproduced plants were thus made at Altadena, California, and about 500 such asexually reproduced plants were raised at San Marino, California.

In all of the asexually reproduced plants the claimed improved variety came true to form.

Figure 1:
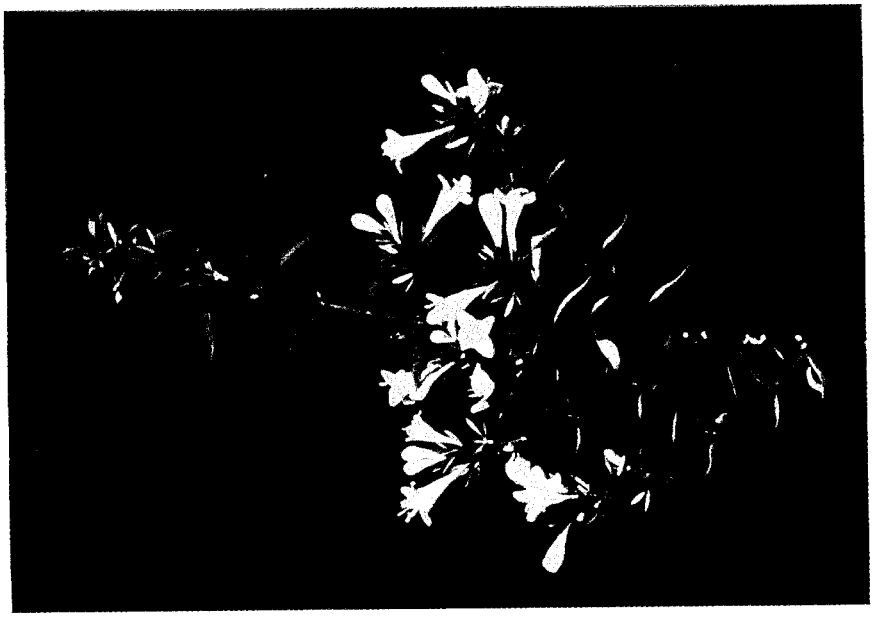
Figure 2:
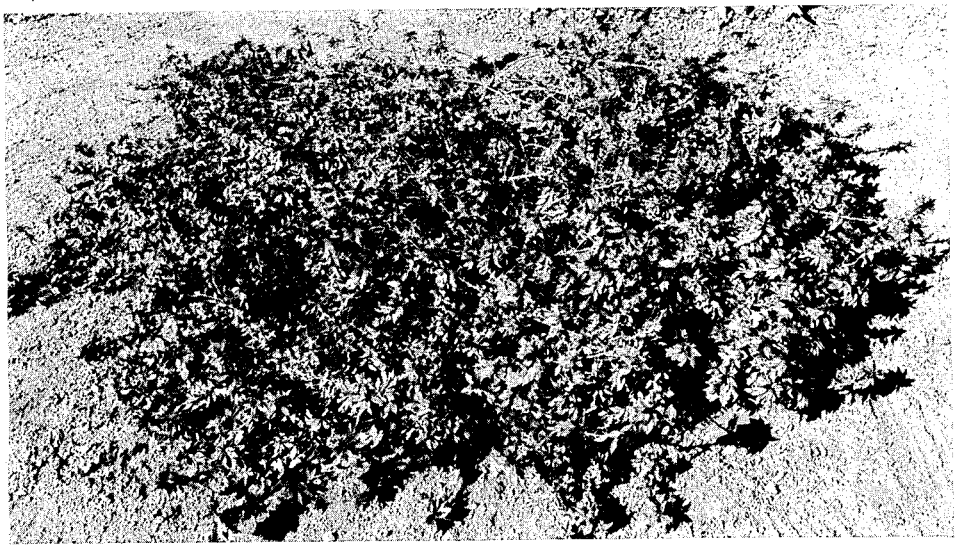

In the accompanying drawings, Fig. 1 is a color photograph showing an enlarged detail view of the flowers and foliage of individual branches; and Fig. 2 is a black and white view showing my bush in its entirety incorporating a large number of the individual branches shown in Fig. 1.

The following is a detailed description of the new variety based upon observations of specimens grown at the locations set forth:

*Leaves.*—Opposite; short petioled; small measuring about ½ to ¾ inch long by about ¼ to ⅜ inch wide; ovate; rounded or attenuate at base; acute tip. Color corresponding to L–4, plate 16, page 55 of Maerz and Paul Dictionary of Color.

The leaves appear on the stems at the nodes from $^3/_{16}$ to ⅜ inch apart which is considerably closer together than in the parent plant, as well as being smaller. Also, the leaves are denser than in the parent plant.

*Flowers.*—In terminal, loose panicles; white; campanulate; about ½ to ¾ inch long; ⅜ to ½ inch wide in open blooms. There is always only one pistil. The color of the stigma is white. There are either two or three stamens. The filaments are white, and the anther color usually corresponds to C–1, plate 51 of Maerz and Paul Dictionary of Color.

The flower has three to five sepals, and the sepal color usually corresponds to H–1 of plate 47 of Maerz and Paul Dictionary of Color. The sepals are between $^3/_{32}$″ and $^3/_{16}$″ in length, and $^1/_{32}$″ to $^1/_{16}$″ wide.

The stems have a tendency to branch at nearly every node, which tendency further serves to distinguish my new variety from the parent plant. The parent plant definitely does not tend to branch at nearly every node. This more frequent branching gives my bush a fuller, denser, more solid appearance than the parent plant possesses.

I claim:

A new and distinct variety of abelia shrub substantially as herein described and illustrated, characterized as to novelty by its exceptionally low spreading prostrate or trailing growth; the dense, opposite short petioled, small, foliage; and smaller size of the flowers.

No references cited.